United States Patent
Hann (10) Patent No.: US 8,011,041 B2
(45) Date of Patent: Sep. 6, 2011

(54) DEVICES FOR PREVENTION OF PRESSURE ULCERS

(75) Inventor: Elly Hann, La Jolla, CA (US)

(73) Assignee: Persimmon Scientific, Inc., La Jolla, CA (US)

( * ) Notice: Subject to any disclaimer, the term of this patent is extended or adjusted under 35 U.S.C. 154(b) by 554 days.

(21) Appl. No.: 12/203,040

(22) Filed: Sep. 2, 2008

(65) Prior Publication Data

US 2009/0070939 A1 Mar. 19, 2009

Related U.S. Application Data

(60) Provisional application No. 60/973,643, filed on Sep. 19, 2007.

(51) Int. Cl.
*A47C 27/08* (2006.01)
(52) U.S. Cl. .............................. 5/652.1; 5/655
(58) Field of Classification Search .............. 5/638, 655, 5/724–725, 952, 652.1
See application file for complete search history.

(56) References Cited

U.S. PATENT DOCUMENTS

| | | | |
|---|---|---|---|
| 3,968,292 A | 7/1976 | Pearman et al. | |
| 3,989,867 A * | 11/1976 | Sisson | 428/132 |
| 4,554,930 A | 11/1985 | Kress | |
| 4,614,000 A | 9/1986 | Mayer | |
| 4,637,819 A * | 1/1987 | Ouellette et al. | 604/369 |
| 4,959,059 A | 9/1990 | Eilender et al. | |
| 4,962,769 A | 10/1990 | Garcia | |
| 5,033,291 A | 7/1991 | Podoloff et al. | |
| 5,103,518 A | 4/1992 | Gilroy et al. | |
| 5,244,716 A | 9/1993 | Thornton et al. | |
| 5,462,519 A | 10/1995 | Carver | |
| 5,636,382 A | 6/1997 | Chopko et al. | |
| 5,787,523 A | 8/1998 | Lindberg | |
| 5,873,137 A | 2/1999 | Yavets-Chen | |

(Continued)

FOREIGN PATENT DOCUMENTS

JP 8327474 A 12/1996

(Continued)

OTHER PUBLICATIONS

International Search Report and Written Opinion for PCT/US08/75047 issued Jan. 29, 2009.

(Continued)

*Primary Examiner* — Fredrick Conley
(74) *Attorney, Agent, or Firm* — Eleanor M. Musick; Procopio, Cory, Hargreaves & Savitch, LLP (57) ABSTRACT

A support surface, such as an underpad, for preventing pressure sores in a patient is a multi-layer textile assembly having a skin contact layer formed from a fabric of synthetic filament yarns woven to provide air permeability and moisture vapor permeability and having a thickness of less than 1 mm. An absorbent middle layer is formed from a breathable microfiber fabric woven to provide for moisture transition from an upper surface of the middle layer to a bottom surface of the middle layer. The skin contact layer and the middle layer are stitched together using a stitching pattern optimized to produce an open pattern with minimal puckering. A bottom layer is formed from a breathable, waterproof fabric woven from synthetic yarn to produce a moisture vapor transfer rate within the range of 5,000 to 20,000 grams per meter squared per 24 hours. The three layers are attached together around their outer edges.

24 Claims, 7 Drawing Sheets

U.S. PATENT DOCUMENTS

| | | | |
|---|---|---|---|
| 6,030,351 | A | 2/2000 | Schmidt et al. |
| 6,131,221 | A | 10/2000 | Yang |
| 6,131,469 | A | 10/2000 | Wortman et al. |
| 6,277,770 | B1 | 8/2001 | Smith, III et al. |
| 6,287,253 | B1 | 9/2001 | Ortega |
| 6,492,434 | B1 | 12/2002 | Barley, Jr. et al. |
| 6,645,887 | B2 | 11/2003 | Kocinec et al. |
| 6,754,919 | B2 | 6/2004 | Leaphart et al. |
| 6,770,581 | B1 | 8/2004 | DeMott et al. |
| 6,799,342 | B1 | 10/2004 | Jarmon |
| 6,889,397 | B2 * | 5/2005 | Rosenberg .................. 5/655 |
| 6,897,781 | B2 | 5/2005 | Cooper et al. |
| 6,953,439 | B1 | 10/2005 | Kabemba |
| 7,030,764 | B2 | 4/2006 | Smith et al. |
| 7,090,647 | B2 | 8/2006 | Mimura et al. |
| 7,146,666 | B2 | 12/2006 | Christofferson et al. |
| 7,152,484 | B2 | 12/2006 | Meyer et al. |
| 7,184,963 | B1 | 2/2007 | Shannon |
| 7,211,709 | B2 | 5/2007 | Shimoe et |
| 2002/0026814 | A1 | 3/2002 | Lee |
| 2002/0148047 | A1 | 10/2002 | Corzani et al. |
| 2003/0089097 | A1 | 5/2003 | Lee et al. |
| 2003/0171954 | A1 | 9/2003 | Guerin et al. |
| 2004/0024375 | A1 | 2/2004 | Litvay |
| 2004/0046668 | A1 | 3/2004 | Smith et al. |
| 2005/0069672 | A1 | 3/2005 | Katsin |
| 2005/0256435 | A1 | 11/2005 | Hess |
| 2005/0273940 | A1 | 12/2005 | Petrosenko et al. |
| 2006/0025686 | A1 | 2/2006 | Ueno et al. |
| 2006/0065060 | A1 | 3/2006 | Ito |
| 2006/0116904 | A1 | 6/2006 | Brem |
| 2006/0282028 | A1 | 12/2006 | Howard et al. |
| 2006/0293613 | A1 | 12/2006 | Fatehi et al. |
| 2007/0004971 | A1 | 1/2007 | Riley et al. |
| 2007/0055545 | A1 | 3/2007 | Maughan et al. |
| 2007/0056096 | A1 | 3/2007 | Assink |
| 2007/0261548 | A1 | 11/2007 | Vrzalik et al. |
| 2007/0277282 | A1 | 12/2007 | Sheppell |

FOREIGN PATENT DOCUMENTS

| | | |
|---|---|---|
| WO | WO9964238 A1 | 12/1999 |
| WO | WO0134080 A2 | 5/2001 |

OTHER PUBLICATIONS

Ho CH et al. The prevention and treatment of pressure ulcers, Phys Med Rehabil Clin N Am, May 2007;18(2):235-53.

Niezgoda JA et al. The effective management of pressure ulcers, Adv Skin Wound Care, Jan.-Feb. 2006;19 Suppl 1:3-15.

Kwiatkowski RJ et al. A closed loop automated seating system, J Rehabil Res Dev, 1993;30(4):393-404.

Meiners T et al. Pressure distribution measurements during use of wheelchairs, Orthopade, Apr. 2001;30(4):208-13.

Brienza DM et al. Seat support surface optimization using force feedback, IEEE Trans Biomed Eng., Jan. 1993;40 (1):95-104.

Okuwa M et al. Measuring the pressure applied to the skin surrounding pressure ulcers while patients are nursed in the 30 degree position, J Tissue Viability, Jan. 2005;15(1):3-8.

Marcellus L. Determination of positional skin-surface pressures in premature infants, Neonatal Netw, Jan.-Feb. 2004;23 (1):25-30.

Sugama J et al. Reliability and validity of a multi-pad pressure evaluator for pressure ulcer management, J Tissue Viability, Oct. 2002;12(4):148-53.

Suriadi et al. A new instrument for predicting pressure ulcer risk in an intensive care unit, J Tissue Viability, Aug. 2006;16(3):21-6.

Rithalia SV et al. Assessment of alternating-pressure air mattresses using a time-based pressure threshold technique and continuous measurements of transcutaneous gases, J Tissue Viability, Jan. 2000;10(1):13-20.

Rithalia SV. Evaluation of alternating pressure air mattresses: one laboratory-based strategy, J Tissue Viability, Apr. 2004;14(2):51-8.

Rithalia SV et al. Assessment of alternating air mattresses using a time-based interface pressure threshold technique, J Rehabil Res Dev, Jun. 1998;35(2):225-30.

Goetz LL et al. Interface pressure characteristics of alternating air cell mattresses in persons with spinal cord injury, J Spinal Cord Med, 2002 Fall;25(3):167-73.

Allen V et al. Measurements of interface pressure between body sites and the surfaces of four specialised air mattresses, Br J Clin Pract, May-Jun. 1994;48(3):125-9.

Fontaine R et al. A quantitative analysis of pressure and shear in the effectiveness of support surfaces, J Wound Ostomy Continence Nurs, Sep. 1998;25(5):233-9.

Patel UH et al. The evaluation of five specialized support surfaces by use of a pressure-sensitive mat, Decubitus, May 1993;6(3):28-31, 34, 36-7.

Cullum N et al. Support surfaces for pressure ulcer prevention, Cochrane Database Syst Rev. 2000;(2):CD001735.

Cumming WT et al. Microprocessor-based weight shift monitors for paraplegic patients, Arch Phys Med Rehabil, Mar. 1986;67(3):172-4.

Grip JC et al. Wheelchair-based mobile measurement of behavior for pressure sore prevention, Comput Methods Programs Biomed, Mar. 1986;22(1):137-44.

Gefen A et al. The false premise in measuring body-support interface pressures for preventing serious pressure ulcers, J Med Eng Technol, Sep.-Oct. 2007;31(5):375-80.

Someya, T. et al., "Conformable, flexible, large-area networks of pressure and thermal sensors with organic transistor active matrixes", Aug. 2005; Proc. National Academy of Sciences 102 (35):12321-12325.

Edlich, RF, et al, "Pressure ulcer prevention", J. Long Term Eff Med Implants, 2004; 14(4):285-304.

* cited by examiner

DEVICES FOR PREVENTION OF PRESSURE ULCERS

RELATED APPLICATIONS

This application claims the priority of U.S. Provisional Application No. 60/973,643, filed Sep. 19, 2007, which is incorporated herein by reference in its entirety.

BACKGROUND OF THE INVENTION

Pressure ulcers can develop in a person who is bedridden, confined to a wheelchair, or otherwise subject to extended periods of immobility. An estimated 1.3 to 3 million patients in the United States have pressure ulcers; incidence is highest in older patients, especially when hospitalized or in long-term care facilities. Both intrinsic and extrinsic factors may be involved in the development of such pressure ulcers. Aging increases risk, in part because of reduced subcutaneous fat and decreased capillary blood flow. Some additional intrinsic factors include impaired mobility, incontinence, skin condition, nutrition, and altered mental status.

Exposure to pressure is one extrinsic factor. When a bony prominence is pressed against a support surface of a bed or a chair under the person's weight, pressure tends to be focused on that prominence. Depending on the type of mattress or cushion, continuous pressure due to immobility can be at least one contributing factor in causing a break in the person's skin, reduced blood flow to that tissue and/or the loss of surface tissue and disintegration and necrosis of epithelial tissue, i.e., an ulcer.

The scope and cost of such pressure ulcers in the United States are significant. Furthermore, no dollar amount can be placed on the cost of human suffering from this debilitating condition.

Implementation of guidelines set forth by the Agency for Health Care Policy and Research (AHCPR) has produced improvements in carefully monitored institutions. These studies demonstrated that with diligent nursing care, many pressure ulcers are preventable. However, with staff/patient ratios typically found in many health care facilities, it may be impractical to expect all aspects of the AHCPR guidelines to be followed for all but high-risk patients. The extent of this problem can only be expected to grow as medical advances prolong the life expectancy of seriously ill patients and as the population over the age of 65 expands.

Medical conditions that do not necessarily involve immobility can also increase the risk of the formation of pressure ulcers or similar types of sores. These sores typically occur in the lower extremities, such as neuropathic ulcers that are frequently associated with diabetes, where sores may form as a result of the patient's reduced sensation and/or circulation in their feet, sometimes leading to amputation of the foot or leg, or even death from infection at the site when a sore goes untreated. Venous ulcers and arterial ulcers can also result from prolonged pressure and ischemia.

Approaches for prevention of pressure sores tend to fall within two broad, but not necessarily mutually exclusive, categories—underpads, pressure redistribution surfaces and electronic sensors and monitoring systems. Among pressure redistribution or support surfaces, proposed solutions include overlays, replacement mattresses, and specialty beds that attempt to reduce the amount of pressure to which tissues are subjected. These approaches tend to vary in effectiveness, practicality of use, economy and maintenance requirements. Most address a few of the problems, but none considers all of the conditions that can be encountered in patient care including shear forces, moisture management, bunching, surface texture, breathability, odor control, durability and launderability.

Current products tend to focus on single-problem solutions, such as absorbent incontinence pads for handling moisture, or pressure re-distribution surfaces to reduce pressure. In order to avoid ruining a mattress or seat cushion, incontinence pads are often backed with non-breathable waterproof material, so that moisture is trapped within the pad. These pads frequently have cotton or synthetic covers and generally do not have moisture-wicking capability, increasing the risk of ulcer formation in an at-risk patient if the pad is not changed promptly when wet. The current industry approach for dealing with the shearing problem is to coat the top layer of the pad with silicone.

A number have support surface improvements have been suggested for reducing the risk of formation of pressure ulcers. U.S. Patent Publication No. 2007/0277282 of Sheppell, entitled "Support for Prevention of Decubitus Ulcers", describes a two-layer pad that is attached at selected portions of the fabric to allow parallel movement between the layers to absorb shearing forces. Examples of the layers are spandex for the top layer and nylon for the second layer. The second layer may also be cotton, wool, felt or any of a number of synthetic or blended fabrics. While shearing forces may be reduced, relative movement among the layers raises the opportunity for bunching, which can create lumps that increase pressure against the skin. Furthermore, there is no provision for drawing and keeping moisture away from the skin. The lack of breathability causes skin warming, which contributes to maceration of the skin.

U.S. Patent Publication No. 2007/0261548 Of Vrzalik, assigned to Kinetic Concepts, Inc., describes a multi-layered support system for prevention of decubitus ulcers which has three layers: a vapor permeable layer, a spacer layer having small air pockets through which air can be pumped, and a third outer layer that is vapor and air impermeable. An aperture is formed through one of the outer layers for connection to an air source. The spacer layer can be open cell foam, polymer particles or similar materials. Layers are bonded together using RF welding, heat sealing, or sonic welding. While the contact layer is vapor permeable, there is nothing to keep the moisture away from the skin, and the outer layer prevents evaporation, so that moisture can be retained within the pad.

U.S. Pat. No. 4,962,769 of Garcia, assigned to Prevent Products, describes a three-layer structure that can be used in diapers for bedridden patients. The inner, skin contact layer is water absorbent. The middle layer provides cushioning in the form of patterns of bubbles, similar to bubble wrap and is mostly water impervious except for bores that allow water to pass through. The outer layer is water impervious. The lack of breathability increases the risk of skin warming.

Other proposed approaches include U.S. Pat. No. 7,211,709 of Shimoe, which describes a multi-layered disposable diaper, and U.S. Patent Publication No. 2007/0056096 of Assink, which describes a multi-layer bed pad which includes an upper layer made from very fine, non-woven polyethylene fibers to provide a smooth, low friction surface. This approach also suffers from non-breathable outer layer.

The second approach to reducing the risk of pressure ulcers is to provide a series of electronic sensors that detect pressure and/or moisture on the patient's body, providing input to a computer monitor which may be used to predict risk conditions or generate alarms based on a patient's history of ulcer development, warning a caregiver that the patient needs to be turned or otherwise attended to. U.S. Pat. No. 6,287,253 of Ortega, assigned to Sabolich Research and Development, describes a computer-implemented pressure ulcer management method that applies electronic pressure sensors directly to locations of a patient's body that are at risk for sores, providing read-outs from the sensors to a computer monitoring system, and generating a signal to indicate when attention is required. U.S. Patent Publication No. 2006/0065060 of Ito, assigned to Pentax Corporation describes a multi-layer mat with an embedded array of electronic pressure sensors for detection of pressure and generation of an alarm to indicate when abnormal pressure is present, notifying the caregiver that a patient needs to be turned to prevent formation of pressure sores. Such systems can be quite costly and generally will be purchased for institutional usage more so that for in home use.

In view of the foregoing, and as an increased number of patients are given home care, there is the need for effective and affordable materials and devices for pressure ulcer management and prevention.

SUMMARY OF THE INVENTION

The present invention addresses one aspect of the aforementioned needs by providing a multi-layered textile assembly that possesses all of the qualities that are important for reducing the risk of pressure sore formation through improved comfort, moisture wicking, breathability, shear reducing, rapid drying and anti-microbial, while being durable, launderable and lightweight.

The multi-layered textile assembly of the present invention may be used as a bed pad, also known as an underpad, for placement on top of a mattress for direct contact with a patient's skin, a mattress cover or seat cushion cover for use in combination with foam or other cushioning layer, or even as a shoe insole liner.

In one aspect of the invention, a support surface is provided for preventing pressure sores in a patient, the support surface comprising a multi-layer composite textile having a skin contact layer formed from a woven fabric of synthetic filament yarns woven to provide air and moisture vapor permeability and a non-shearing surface, with a thickness of less than 1 mm, the skin contact layer having an upper, skin contact surface and a bottom surface; an absorbent middle layer abutting the bottom surface of the skin contact layer, the middle layer formed from a breathable microfiber fabric woven from synthetic fibers having a cross-sectional shape that includes a plurality of voids for generating a capillary effect for moisture transition from an upper surface of the middle layer to a bottom surface of the middle layer, wherein the skin contact layer and the middle layer are stitched together using a stitching pattern that is optimized to produce an open pattern with minimal puckering; and
a bottom layer attached to the skin contact layer and the middle layer at a peripheral edge of each layer, the bottom layer formed from a breathable, waterproof fabric having a thickness of less that 1 mm that is woven from synthetic yarn to produce a moisture vapor transfer rate within the range of 5,000 to 20,000 grams per meter squared per 24 hours. In one embodiment, the stitching pattern by which the upper two layers are assembled comprises a plurality of straight and curved lines, wherein no lines cross over other lines.

In an exemplary embodiment, a three-layer textile assembly includes an upper layer, typically for direct skin contact or contact with the patient's gown or pajamas, which is a thin (<1 mm), lightweight (~2.5 ounce) polyester that is breathable, non-shearing, anti-microbial, moisture wicking and quick drying. Examples of appropriate fabrics for this upper layer include the fabric described in U.S. Pat. No. 6,277,770 of Smith, (incorporated herein by reference) which is assigned to Precision Fabrics, Inc. (Greensboro, N.C.), or similar fabrics made by Precision Fabrics or by Teijin Fibers Ltd. (Tokyo, Japan), such as Teijin's NANOFRONT™ polyester fiber. The middle layer of the assembly is an absorbent, breathable microfiber layer that is flexible and conforms to the body, with a thickness on the order of 1.5 to 3.5 mm, more preferably less than 3 mm and most preferably less than 2 mm. A preferred microfiber material has a density of 180-340 gm/m$^2$, such as the microfiber materials used in the AQUIS® products available from Britanne Corporation or SILVERSTAR2000 microfiber fabric available from Silverstar Corporation Ltd. (Welcron Company Ltd.) (South Korea). Such microfiber fabrics absorb liquid faster than cotton by the capillary effect created within tiny spaces between the threads and are able to dry rapidly by communicating the liquid away from the source. The outer layer of the assembly is a thin, lightweight, waterproof, breathable fabric such as the polyester or nylon fabrics coated with polyurethane. Such fabrics are available from Young Poong Filltex Co. Ltd. (South Korea), Formosa Taffeta Company, Ltd. (Taiwan), or PORELLE® membranes available from PILMembranes Ltd. (formerly Porvair International) (U.K.)

A factor that affects the smoothness and comfort of the surface is the assembly method used for combining the multiple layers and finishing the edges of a pad or cushion. The assembly method also effects launderability and drying time. In the preferred embodiment, the multi-layer fabric is stitched using a smooth polyester thread to form a quilted pattern with features and dimensions that are optimized to minimize puckering or bunching, minimize washing and drying time, while maximizing comfort, durability and breathability. Seams, if any, should be free of puckering and are preferably limited to those used for finishing the outer edges of the pad, or the sides of a cushion or mattress cover, so that the skin contact surface is substantially seamless. In one embodiment, a friction-enhancing strip, such as silicone or other rubber-like synthetic material, may be formed or attached to selected areas on the outer edges of the bottom side of a pad to facilitate gripping by a care giver when the patient is moved or bedding is changed. The stitching or other attachment method used to apply the grip strip should have minimal impact on the smoothness of the upper skin contact surface.

BRIEF DESCRIPTION OF THE DRAWINGS

FIG. 1a is magnified to show detail. FIG. 1b is a second embodiment of the support surface showing a different stitching pattern.

DETAILED DESCRIPTION OF PREFERRED EMBODIMENTS

According to the present invention, a support surface for prevention of pressure ulcers is a multi-layer composite fabric which is assembled to overcome most of the important factors that are involved in formation of such ulcers. Each layer addresses at least one specific risk factor for pressure ulcer formation while the assembly as a whole enhances these features, at the same time taking into consideration the qualities that make such a product easy to manufacture and affordable such that it can be made widely available for both institutional and home use.

In the preferred embodiment, a three-layer assembly includes an upper layer, typically for direct skin contact, which is a thin (<1 mm, preferably less than 0.5 mm), lightweight (~2.5 ounce) polyester that is breathable, non-shearing, anti-microbial, moisture wicking and quick drying. Examples of appropriate fabrics for this upper layer include the fabric described in U.S. Pat. No. 6,277,770 of Smith, (incorporated herein by reference) which is assigned to Precision Fabrics, Inc. (Greensboro, N.C.), or similar fabrics made by Precision Fabrics, such as those sold under the trademark DERMATHERAPY™, or by Teijin Fibers Ltd. (Tokyo, Japan), such as Teijin's NANOFRONT™ polyester fiber.

The thin, lightweight upper layer conforms well to the user's body and dries quickly. The fabric used for the upper layer has a combination of air porosity (to allow venting through the fabric's planar surface), moisture vapor transport (to enhance comfort), fabric flexibility (also a comfort-enhancing property), extremely small pore size, a non-shearing surface (for reduced friction), and durability to laundering. The fabric thickness is less than 1 mm, with a typical thickness of 0.2 mm. This combination of properties is provided by weaving fine-denier synthetic filament yarns (polyester or nylon-polyester blend) into a tight plain-weave construction with post finishing processes that maximize fiber coverage and filtration efficiency. Because the fabric is woven from continuous synthetic filament and/or spun yarns, there are no short fibers to irritate skin or become embedded in a wound or sore. The fabric is finished to provide a fabric with a mean pore size of 4 to 10 microns, an air permeability of 0.5-30 cubic feet per minute per square foot of fabric at 0.5 inches of water ("cfm," measured by Federal Test Method Standard (FTM) 5450, also known as ASTM D-737), a mean fabric flexibility of 0.5 to 6.5 grams (bending resistance), and a moisture vapor permeability in excess of 800 g/m² per 24 hours. The coefficient of friction for the fabric is on the order of 0.5, which is approximately one-half of the coefficient of friction for a cotton or polyester/cotton blend with roughly the same fiber and weave. Any suitable antimicrobial or fluorochemical finish can be used; such finishes are known in the art (e.g., U.S. Pat. No. 4,822,667). An example of a suitable antimicrobial finish that can be applied is a compound of 3-(trimethoxysilyl)-propyidimethyloctadecyl ammonium chloride (DOW CORNING 5700). This finish protects the fabric against bacteria and fungi, and inhibits the growth of odor-causing bacteria.

As shown in Table 1, compared with currently commercially-available products, the preferred skin contact layer provides all of the desired qualities for prevention of pressure ulcers.

TABLE 1

| | Fabric | | | |
| --- | --- | --- | --- | --- |
| Feature | Present invention - top layer | Disposable (e.g., MEDLINE ULTRASORBS ™) | 100% Cotton (e.g., MEDLINE flannel soaker) | 100% Polyester (e.g., DURO-MED 3-ply quilted) |
| Moisture wicking | yes | yes | no | no |
| Breathable | yes | yes | yes | no |
| Quick Drying (<5 min.) | yes | NA | no | no |
| Anti-microbial | yes | NA | no | no |
| Body conforming | yes | no | no | no |
| Non-shearing | yes | yes | no | no |
| Weight | light | light | heavy | heavy |
| Thickness | <1 mm | <1 mm | 2 mm | 3-4 mm |
| Washable | yes | no | yes | yes |
| Recyclable potential | yes | no | NA | NA |

The light, thin top layer is particularly advantageous for purposes of quilting, since the thicker the fabric, the greater the chance of puckering and bunching when quilted, which can form pressure points against the patient's skin.

Figure 7:
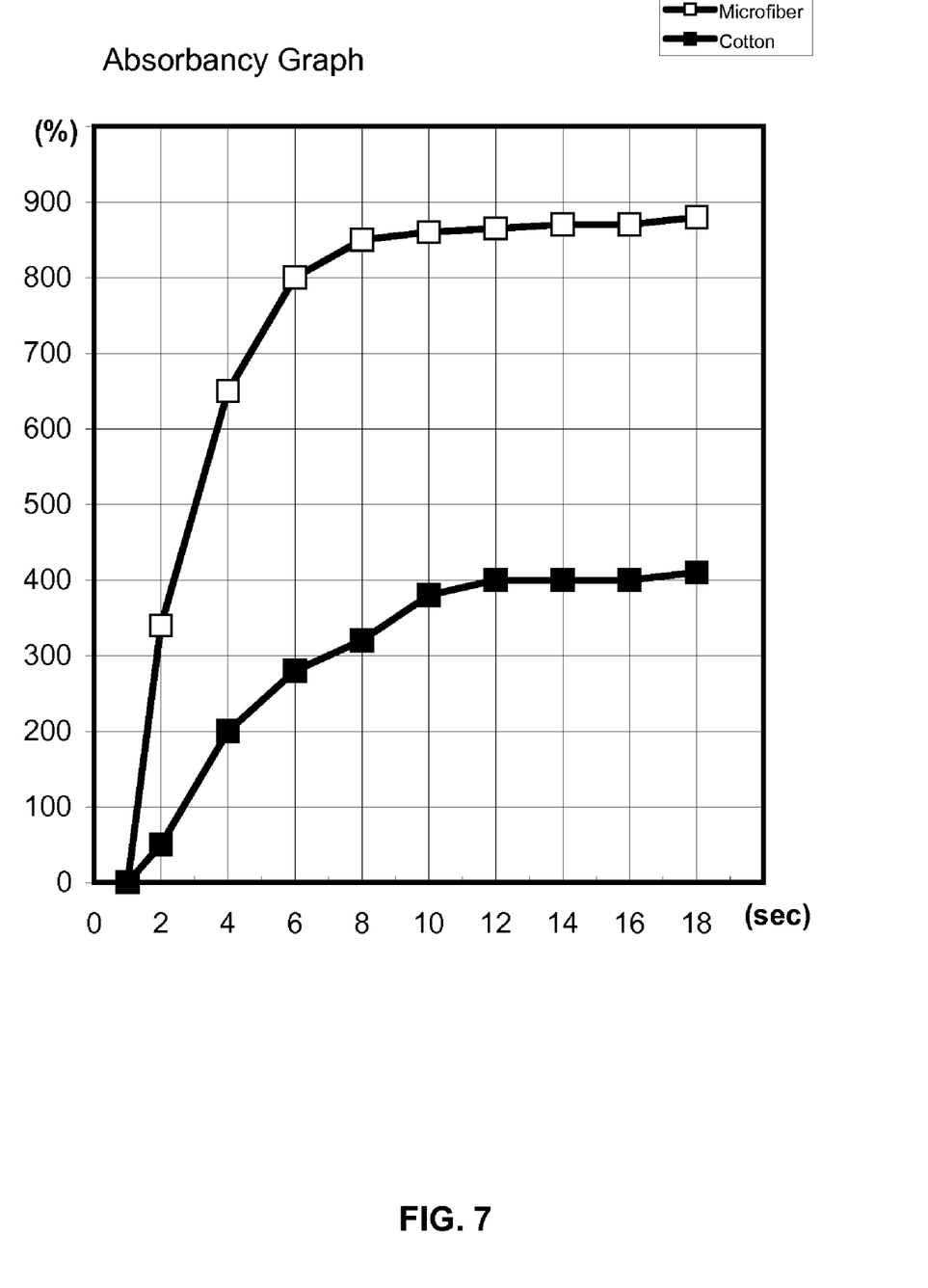
FIG. 7 is a graph comparing the absorbency of microfiber versus cotton.

The middle layer of the assembly is an absorbent, breathable polyester microfiber that is flexible and conforms to the body, with a thickness on the order of 1.5 to 3.5 mm, more preferably less than 3 mm and most preferably less than 2 mm. A preferred microfiber has a density of 180-340 gm/m², such as the microfiber materials used in the AQUIS® products available from Britanne Corporation, or SILVERSTAR2000™ microfiber fabric available from SilverStar Corporation Ltd. (Welcron Company Ltd.) (Seoul, South Korea) (see U.S. Pat. No. 6,381,994 of Lee, which is incorporated herein by reference). Such microfiber fabrics are formed by weaving synthetic filaments or fibers that have many channels extending along the fiber length, thus creating fine voids within their cross-sections. The microfiber fabrics are able to absorb liquid faster and in greater volume than cotton due to the capillary effect produced by the voids and channels within the fibers and, thus, are able to dry rapidly by communicating the liquid away from the source. FIG. 7 is a graph of the relative absorbency of microfiber and cotton with time, showing that the microfiber has a moisture absorbing capacity more than two times that of cotton.

Table 2 provides a comparison of relevant characteristics of the absorbent middle layer of the multi-layer fabric of the preferred embodiment of the present invention to currently commercially-available products.

TABLE 2

| Feature | Fabric | | | |
|---|---|---|---|---|
| | Present invention - middle layer | Disposable (e.g., MEDLINE ULTRASORBS ™) | MEDLINE polyester soaker | 100% Polyester DURO-MED |
| Absorbs fluids | yes | yes | no | no |
| Washable | yes | no | yes | yes |
| Body-conforming | yes | no | no | no |
| Breathable | yes | no | no | no |
| Discourages microbes | yes | NA | NA | NA |
| Thickness | 2 mm | irregular (absorbent gel forms clumps) | 3-4 mm | 3-4 mm |
| Recyclable potential | yes | no | NA | NA |

The outer layer of the assembly is a thin, lightweight, waterproof, breathable fabric such as the polyester or nylon, i.e., synthetic, fabrics coated with polyurethane available from Young Poong Filltex Co. Ltd. (South Korea), Formosa Taffeta Company, Ltd. (Taiwan), or PORELLE® membranes available from PILMembranes Ltd. (formerly Porvair International) (U.K.).

TABLE 3

| Feature | Fabric | | | |
|---|---|---|---|---|
| | Present invention - middle layer | Disposable (e.g., MEDLINE ULTRASORBS ™) | MEDLINE polyester soaker | 100% Polyester DURO-MED |
| Waterproof | yes | yes | yes | yes |
| Breathable | yes | yes | no | no |
| Body-conforming | yes | no | no | no |
| Washable | yes | no | yes | yes |
| Weight | light | light | heavy | heavy |
| Thickness | <1 mm | <1 mm | 2-3 mm | 2-3 mm |
| Recyclable potential | yes | no | NA | NA |

Exemplary characteristics of a preferred fabric for the outer (bottom) layer of the inventive multi-layer support surface include a fabric weight on the order of 80-100 gm/m$^2$ that is waterproof and breathable. The breathability of the outer layer is measured according to moisture vapor transfer rate (MVTR), expressed in units of grams/meter$^2$/day. For purposes of the present invention, a MVTR range of 5,000 to 20,000 g/m$^2$/day is preferred. Table 4 below provides a comparison of the breathability of three different fabrics from Young Poong and Formosa after applying 2 ml of water to the fabric. The degree of dryness was tested on the underside of the fabric, which would correspond to the moisture to which a mattress beneath the fabric would be exposed. The MVTR values were provided by the manufacture and were not independently confirmed.

TABLE 4

| | Product (MVTR) | | |
|---|---|---|---|
| Hr:Min after applying water | FILLTEX ™ (7,000 g/m$^2$/day) | FORMOSA BLUE (7,000 g/m$^2$/day) | FORMOSA YELLOW (10,000 g/m$^2$/day) |
| 0:00 | 80% dry | 80% dry | 80% dry |
| 0:05 | 85% dry | 85% dry | 85% dry |
| 0:10 | 90% dry | 90% dry | 90% dry |
| 0:15 | 95% dry | 95% dry | 95% dry |
| 0:45 | 98% dry | 98% dry | 98% dry |
| 2:30 | Completely Dry | Completely Dry | Completely Dry |

The tests indicated that MVTR ratings of 7,000 and 10,000 g/m$^2$/day were equally effective in drawing away the moisture at a desired rate. The corresponding information for the PORELLE® fabric was not available because it was determined to be relatively non-breathable, suitable only as a waterproof layer.

A factor that affects the smoothness and comfort of the surface is the assembly method used for combining the multiple layers and finishing the edges of a pad or cushion. The assembly method and materials also affect launderability and drying time. For example, a cotton thread tends to have a heavier weight, less give (stretchability) and a longer drying time. In the preferred embodiment, the multi-layer fabric is stitched using a smooth polyester thread. The polyester thread is stronger, lighter, and faster drying with better give. The top two layers of the multi-layer assembly were stitched to form a quilted pattern shown in FIG. 1a, with features and dimensions that are optimized to minimize puckering or bunching, minimize washing and drying time, while maximizing comfort, durability and breathability.

In a comparison of stitch length, a 1.5 mm stitch using polyester thread produced significant puckering with taut stitches, while a 2.5 mm stitch eliminated all puckering, with all of the stitches lying flat. The longer stitch produced a quilted assembly that was smoother to the touch with faster wash and dry times. The stitch tension was also optimized for producing the smoothest possible finish. Using a Towa Bobbin Case Tension Gauge (manufactured by Towa Industrial Company, Ltd. of Japan), a tool that is well known among quilters, the tension was optimized to minimize puckering and improve smoothness of the quilted surface. A tension of 20 gf (gram-force), or 200 milliNewtons, was found to produce more puckering, while 18 gf (180 mN) provided a smooth surface with no puckering.

Figures 2A, 2B:
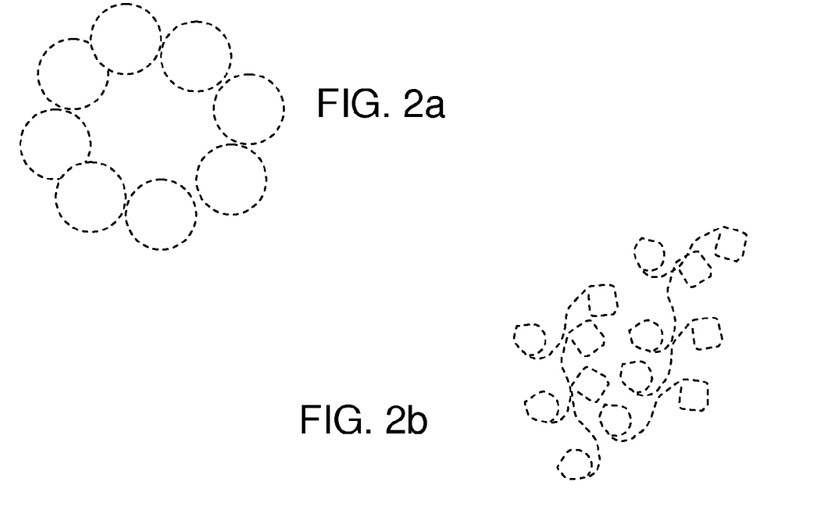
FIGS. 2a-2d are diagrammatical views of alternative stitching patterns for a multi-layer support surface.
Figures 2C, 2D:
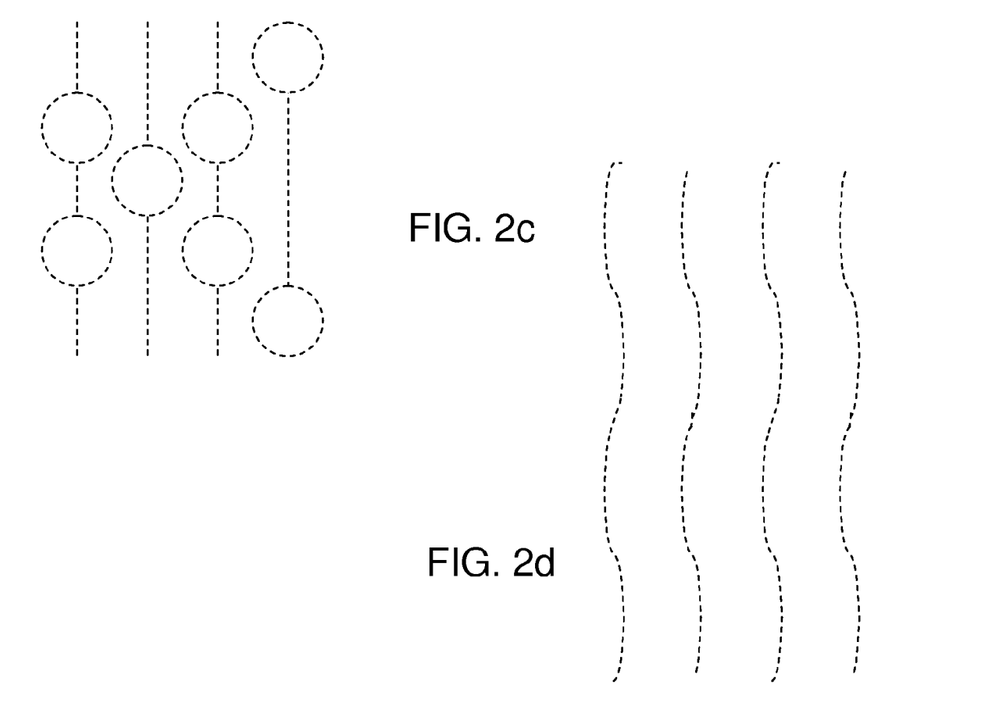

The quilting patterns used to combine the upper two layers of the multi-layer assembly were evaluated for a number of qualities including aesthetic appeal, comfort, bunching, washability and drying rate, fabric longevity and commercial manufacturability. The different patterns considered are shown in FIGS. 2a-2d: FIG. 2a shows a series of attached rings; FIG. 2b, a continuous scroll pattern, FIG. 2c, detached rings with parallel lines, and FIG. 2d shows parallel wavy lines. Table 5 below provides the results of this comparison.

TABLE 5

| Qualities | Pattern | | | |
|---|---|---|---|---|
| | Attached rings with free spaces (FIG. 2a) | Continuous scroll (FIG. 2b) | Detached rings & parallel lines (FIG. 2c) | Parallel, continuous wavy lines (FIG. 2d) |
| Uniqueness | yes | no | yes | no |
| Sense appeal | poor | yes | yes | yes |
| Washability | good | poor | good | good |
| Ease of drying | good | poor | good | good |
| Bunching | significant | no | no | no |
| Fabric Longevity | good | poor | good | good |
| Manufacturability | no | no | no | yes |

The size of the quilted features, i.e., the distance to the closest stitching, was found to impact bunching, moisture trapping and drying time. For the ring patterns, ring diameters of 25 mm (1 inch) were found to produce more puckering, more moisture trapping and longer drying time compared to rings of 50 mm (2 inch) diameter. However, if much larger diameter rings were used, there was an increased risk of movement between the upper and middle layers that could cause bunching when the patient moves. Generally, a ring diameter of 25-50 mm can be used. The separation between adjacent rings is determined in part by the desired pattern, but as indicated in Table 5, abutting circles resulted in significant bunching of the fabric. In the preferred embodiment, ring diameters of about 45 mm are used. A separation on the order of 10 mm between the closest neighboring circles was used. Similarly, the distance between parallel lines, both the straight lines of FIG. 2c and the wavy lines of FIG. 2d, should generally be within the range of 25-50 mm and in the exemplary embodiment was selected as about 45 mm.

Figure 1A:
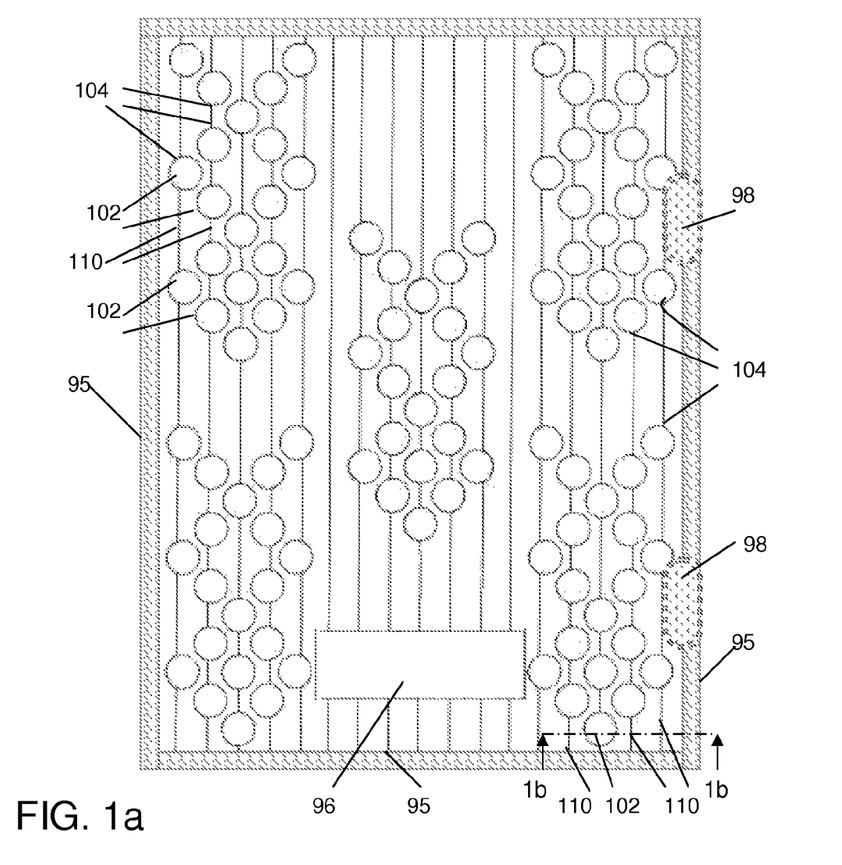
FIGS. 1a and 1b are diagrammatical top and cross-sectional views, respectively, of a first embodiment of a multilayer support surface for prevention of pressure sores.

FIG. 1a illustrates the first pattern with circles and parallel after optimization of the quilting pattern and stitching parameters. The combination of parallel lines 110 and circles (rings) 102 provides an interesting, aesthetically pleasing pattern that provides a combination of horizontal and vertical connectivity (viewing as oriented in the figure) between the upper two layers. The circles are arranged in short, angled lines, with two adjacent circles at approximate 45 degree angles to each other. The parallel lines do not pass through the circles, but end on one side and resume on the opposite side of the circle, so that one stitch line does not cross another. In general, while stitch lines may come together to define an intersection point 104, they preferably will not be allowed to cross, thus avoiding locations of high stitch density that could negatively impact drying time as well as increasing the chance of puckering. The pattern is repeated to produce a two-layer assembly that eliminates the possibility of movement between the layers while remaining sufficiently open to minimize drying time. This quilting pattern had all of the desirable performance features, however, the complicated design is difficult to commercialize on a large scale, i.e., in an automated assembly line, because it requires a single-needle assembly process. As a result, the wavy line pattern of FIG. 2d and FIG. 8a was selected for commercialization. This pattern should follow the general rules discussed above relative to the design of FIG. 2c—the separation between adjacent lines 200 should be within the range of 25-50 mm, the stitch tension and length should be a previously specified, and no two lines should cross because of the possibility of puckering around that point.

Figure 1B:
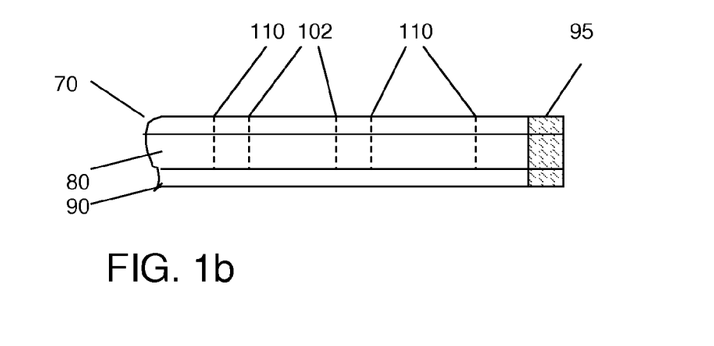

FIG. 1b shows the three layer structure of the inventive support pad. The first layer 70 is the contact layer, second layer 80 is the absorbent layer, and third layer 90 provides the waterproof, breathable backing layer. Only layers 70 and 80 are quilted together. Bottom layer 90 is attached only around its edges so as not to destroy the benefits of the waterproof layer. The stitching at the periphery of the support surface that is to be used as a bed pad or other flat pad is as flat and smooth as possible. In the preferred embodiment, an overlock stitch 95, which may be single thread or, preferably, multi-thread overlock, is used to simultaneously attach the layers and finish the edges. Alternatively, the upper layer may be cut slightly larger than the middle and bottom layers so that it extends beyond the edges of the lower layers. This excess fabric is then folded over and sewn, either with a straight stitch, similar to that used for the quilting, or an overlock stitch may be used. This assembly method is generally not commercializable due to the difficulty in repeatably aligning the different sizes of fabric. If the support surface is being assembled into a cushion cover or pillowcase, inside seams finished to prevent bunching should be used.

Referring again to the embodiment shown in FIG. 1a, at the bottom of the assembly is a rectangular box 96 formed by stitching four straight lines within which is located the product trademark or logo. The stitching used for the box and the logo is the same as that used to form the quilted pattern. As described above, so that the lines of stitching do not cross, the parallel lines 110 terminate on one side of the box 96 and resume at the other side of the box. Even in everyday clothing, tags can be a source of discomfort. By embroidering the trademark as part of the overall design, the need for tags to identifying the source of the goods is eliminated.

In one embodiment, a friction-enhancing strip, such as silicone, rubber or suede, may be formed or attached to areas on the outer edges of the bottom side of a pad to facilitate gripping by a care giver when the patient is moved or bedding is changed. FIG. 1a shows a pair of grips 98 (dashed lines) sewn onto one edge of the pad, while FIG. 5b shows a continuous strip of silicone or rubber running along two sides of the pad. The grips can be placed on all four edges, on two, opposing edges, or along one edge only. The stitching or other attachment method used to apply the grip strips should have minimal impact on the smoothness of the upper skin contact surface and preferably will be located well away from where the patient will be positioned. In an alternate embodiment, grips can be formed by deposition of an epoxy, rubber, or synthetic polymer directly onto the fabric, preferably on the bottom of the third layer, to form a flexible strip that can produce sufficient strength and surface friction to facilitate gripping.

The total combined thickness of the multi-layer assembly of the present invention is on the order of 2-5 mm, preferably at the lower end of the range. The minimal thickness enhances the assembly's ability to conform comfortably to the patient's body. It also provides a pad that is easy to launder and dries quickly. Table 6 below provides a comparison of the moisture wicking capability of a multi-layer pad made according to the present invention, which is sold under the trademark EPIBI™, relative to several commercially-available bed pads and underpads. The amount of water used in the test was 200 mL. "Time" refers to the amount of time that had passed after the water was poured on the top layer of the pad.

TABLE 6

| | Product | | | |
|---|---|---|---|---|
| Time/Quality | EPIBI (Present invention) | Disposable (MEDLINE ULTRASORBS ™) | MEDLINE cotton soaker | 100% Polyester DUROMED |
| 1 min. | | | | |
| Moisture wicking | Wet | Wet (fluid puddles before wicking into porous channels) | Wet; fluid puddles | Wet; fluid puddles |
| Surface texture | Smooth | Smooth | Rough | Rough |
| Breathable | Yes | Yes | No | No |
| Waterproof | Yes | Yes | Yes | Yes |
| 10 min. | | | | |
| Moisture wicking | Damp | Dry | Wet; fluid puddles | Wet; fluid puddles |
| Surface texture | Smooth | Smooth | Rough | Rough |
| Breathable | Yes | Yes | No | No |
| Waterproof | Yes | Yes | Yes | Yes |
| 22 min. | | | | |
| Moisture wicking | Damp/Dry | Damp/Dry | Wet | Wet |
| 30 min. | | | | |
| Moisture wicking | Damp/Dry | Damp/Dry | Wet | Wet |
| Washable | Yes | No | Yes | Yes |
| Recyclable potential | Yes | No | NA | NA |
| Dry cycle after 20 min. in home dryer | 90% dry with small patches of dampness in tightly stitched areas | N/A | Damp | Very damp |

It was also noted that the disposable product had large porous channels in the top surface, which allowed moisture to escape towards the skin for at least four hours.

The multi-layer textile assembly of the present invention is optimized to provide the features appropriate for minimizing the risk of development of pressure ulcers by a patient using a pad made from the assembly. In addition to being moisture wicking, breathable, flexible and non-shearing, an important feature of the assembly is its extremely light weight compared to other commercially-available products. A bed pad having the commonly-used dimensions of 81 cm (32 in.) by 69 cm (27") constructed according to the present invention weighs only 9 ounces, compared to the 20 ounce weight of a conventional cotton or polyester bed pad of the same dimensions. In addition to being more conformable to the patient's body, and therefore, more comfortable, the inventive pad can significantly reduce laundry costs. In an institutional setting, the cost of laundering linens is calculated in terms of weight per average patient day. Because the inventive pad weighs less than half the weight of the most widely used bed pads, the linen costs incurred by hospitals, nursing homes and hospices will be dramatically reduced. In addition, the amount of energy and water consumed during laundering will be significantly reduced.

Bed pads made from the multi-layer composite fabric of the present invention have been evaluated by patients and medical professionals, including nurses and surgeons, and praised as a major advancement in patient care. By addressing each of the many problems that are encountered with patient bedding, a novel pad has been developed that can improve the health and comfort of patients undergoing treatment in a wide range of medical fields. In addition to providing an important tool for pressure ulcer treatment and prevention in at-risk patients, other medical areas that can benefit from the improved comfort, breathability, moisture wicking capability and many other features of the composite fabric include wound care, burn treatment, and labor and delivery.

In another aspect of the invention, devices are disclosed for sensing and monitoring one or more conditions related to the health of a patient and especially related to the development, prevention and treatment of pressure ulcers and similar sores. The present invention particularly provides a novel and improved medical sensor and system and method of monitoring one or more pressure sensitive areas of a human body.

The present invention provides real-time monitoring of pressure status over time, whereby at-risk patients requiring immediate intervention can be quickly identified. The preferred embodiment also offers the advantage of relatively inexpensive disposable sensors that safely monitor exposure time to pressure.

In an exemplary embodiment, a flexible array of pressure transducers is encased in a protective cover. A bed pad having a similar multi-layer structure to that described above can be used in conjunction with the sensors described below.

Figure 3:
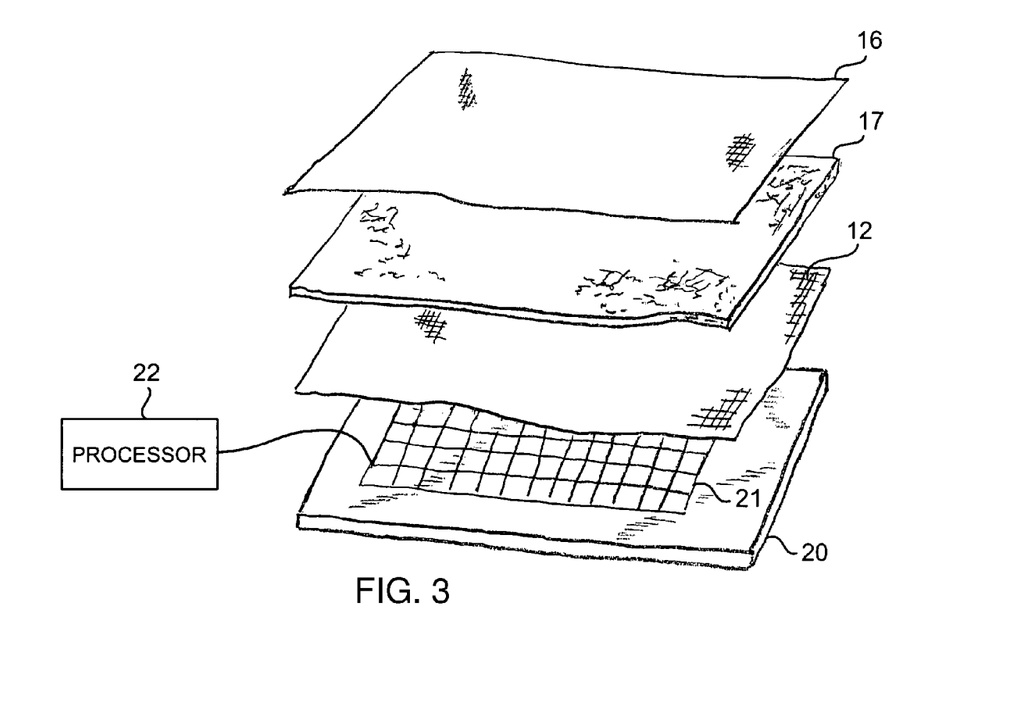
FIG. 3 is a perspective, partially exploded view of an embodiment of the invention with a pressure sensing array.
Figure 4:
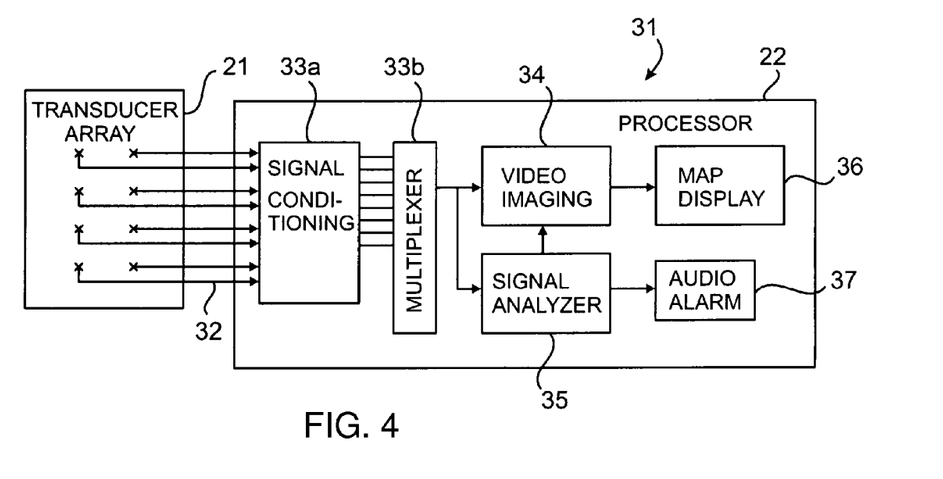
FIG. 4 is a block diagram of the electronic components for generating, receiving and processing signals.

The basic components of the bedding system with pressure monitoring sensors according are illustrated in FIG. 3 and include an optionally antimicrobial treated, porous cloth 16 attached over a layer 17 of moisture-absorbing material backed by a waterproof barrier 12. Underneath the barrier is an array 21 of pressure transducers laid on top of a cushioning pad 20. The processor 22 used for collecting the signals from the sensors in the array and for executing the software for analyzing the data may be a standard personal computer programmed according to techniques known to those skilled in the data processing arts. The software will preferably include a subroutine for generating a display map on a graphical interface showing the various pressure points along with a variety of warning and alarm indicators when risk conditions for pressure ulcers are present.

In an exemplary embodiment, the top surface 16 of the underpad is a lightweight, breathable, flexible, anti-microbial, non-cotton material that wicks away moisture, such as that described previously with reference to FIGS. 1a and 1b. Alternatively, it may be formed from disposable materials based on a combination of cellulose and synthetic fibers. The absorptive layer 17 of the underpad is formed from a thin microfiber fabric that is highly flexible and wick moisture away from the upper layer so as to keep the top surface layer dry. This avoids the problem of typical disposable pads, which become stiff when they get wet. The waterproof layer 12 on the bottom is a thin, breathable, highly flexible material coated with polyurethane to prevent moisture from entering the electronics of the sensors as well as the mattress or chair cushion below.

An embodiment for use with chairs, including wheelchairs, a cushioned seat pad includes extra cushioned overhangs that extend beyond the front edge of the chair at the points where the legs would be extending away from the seat surface, so that the cushions angle down when the chair is in use. This extra cushioning protects the backs of the patient's thighs from the edge of the chair, which can interfere with circulation below the contact points. The thickness of the chair pad increases on both sides of a front-to-back centerline so that additional cushioning is located below the ischial tuberosity, aka, the Sitz bone. The bottom surface of the cushion has a generally rough texture so that friction is generated between the top of the chair seat and the bottom of the cushion.

Preferably, the cushion will include a cover made according to the inventive support surface. The cover should be removable for washing. The cushion can formed from a multi-layered material having alternating layers of a flexible, resilient layer with shock absorbing qualities (similar to common yoga mats) and a molded pad of flexible, resilient material. The first layer may be a foam material that is sufficiently open cell to permit air to be retained within the material until the material is compressed. The second layer may be formed from a material that has greater density than the foam layer, and may include a gel filling for shock absorption. This second layer consists of a flat sheet with integrally formed ribs extending from both the top and the bottom surfaces of the flat sheet. The ribs are angled in such a way that a cross-section of the layer has the appearance of a herringbone pattern. Depending on the material used to make the second layer, each rib will have air or gel trapped within the ribs that is squeezed out of the rib when a weight is applied. The angled orientation of the ribs serves to reduce the shear factor that in conventional pads contributes to pressure ulcers. Multiple alternating layers of each of the two layers can be used to produce the cushion. The number of layers can be adjusted according to the patient's weight.

For use with bedridden or wheelchair-bound patients, the sensor array is embedded in a resilient protective cover that is surrounded by an envelope of impermeable material that can be releasably attached to the undersurface of a multi-layer pad, as shown in FIG. 3. The pad comprises a sheet of permeable cloth, a moisture-absorbing material, a waterproof material and, optionally, a pressure re-distribution surface such as resilient foam or a gel-filled pad. Electrical connection to the sensor array is provided by a cable connected to a processor, or by wireless (RF) transmission.

In one embodiment, a sensor array is embedded in a thin layer of resilient, flexible material formed in the shape of a foot pad shoe liner. An exemplary liner is disclosed in U.S. Pat. No. 5,033,291, which is incorporated herein by reference. The sensors detect real-time pressures against the boney prominences on the foot and generates signals corresponding to the pressure. Signals from the sensor array can be connected to a microcontroller that controls a LED readout on the exterior of the shoe to provide feedback to the wearer to warn of excessive pressure against one or more locations on the foot, which can be used as an advisory to remove or change the shoes, or to rest the feet. Alternatively, the sensor array is connected to a wireless transmitter that transmits a signal to a receiver and microcontroller that can be carried in or on the user's clothing to activate a visual or audible alarm to notify the user that pressure has exceeded a pre-determined pressure for a pre-determined time period.

In another embodiment, an array of sensors is embedded in a sleeve that can be inserted into or incorporated in a stocking that extends at least part way up the lower leg for monitoring pressure generated within varicose veins, for treatment and/or prevention of venous ulcers. The sensor array provides input to a microcontroller which in one application generates a display or alarm indicating increased pressure and possible venous congestion that could lead to ulceration. The patient or caregiver could then activate electronic muscle stimulators to cause the surrounding muscles to contract, as if the patient were walking or flexing the ankle, to alleviate the pressure and restore normal flow. Alternatively, mechanical compression can be applied by a pneumatic or hydraulic pump. In another variation, electronic stimulators can be embedded in the sleeve and connected to the microcontroller, which will activate the stimulators in response to an increase in the detected pressure at a location on the leg. The patient could wear the sleeve/stocking when they are awake and sitting in a chair or wheel chair, or even when walking.

Other embodiments of the pressure detecting sensor array can be embedded in a protective flexible material that has been molded or otherwise configured in thin cup-like shapes that conform to and partially encompass a patient's heels or elbows. A textile cover would be placed against the skin for comfort.

In one implementation, the sensors in the array are relatively inexpensive disposable sensors that are embedded in a disposable sheet, such as those disclosed in U.S. Pat. No. 5,033,291 mentioned above.

Figure 5A:
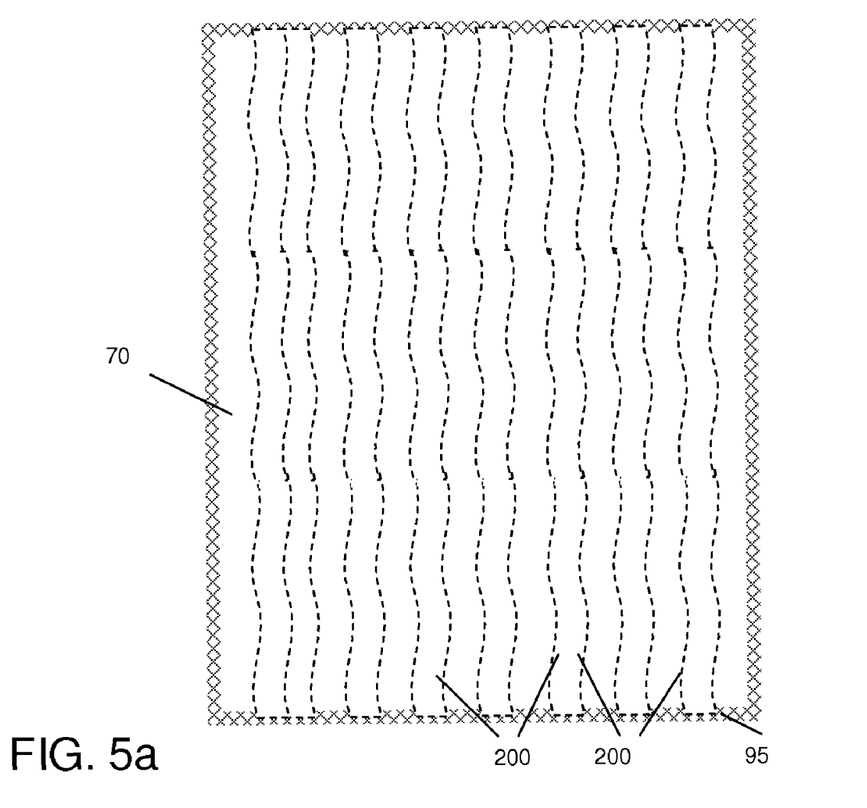
FIGS. 5a and 5b are top and bottom views of a second embodiment of the support surface FIGS. 6 a-c are curves illustrating different algorithms for use in monitoring of a patient.
Figure 5B:
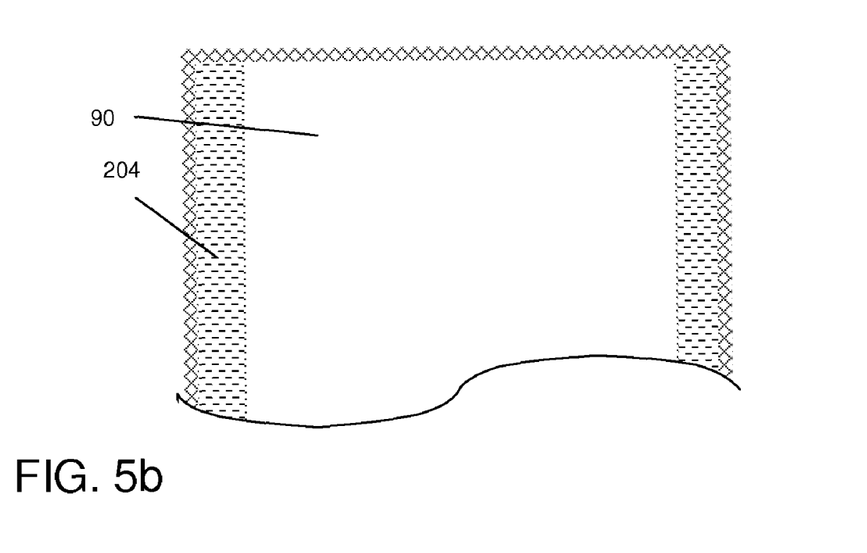

Referring to FIG. 5, the electronic portion 31 of the invention will be described. The pressure value signals 32 generated by the transducer array 21 are led to a signal conditioning unit 33a before entering a multiplexer 33b, the output of the multiplexer is then provided to a video imaging unit 34 and to a signal analyzer 35. The video imaging unit generates a video signal which is used by a video monitor to provide a display 36 of all the pressure points. The signal analyzer is programmed to detect pressure points that exceed a preset limit as well as pressure points of a given level that last for more than a preset limit of time. The results of the analysis may also be fed to the video imaging system and displayed as a visual alarm as part of the mat display 36. The analysis results may also be used to trigger an audio alarm 37 when excessive conditions have been identified by the signal analyzer.

The entire electronic portion 31 including the transducer array 21 data processing components and alarm indicators can be implemented with a pressure-monitoring system such as the one available from Tekscan, Inc. of South Boston, Mass., or XSensor Corporation of Calgary, Canada.

In one embodiment, the signals generated by the sensors in the array are converted by the signal analyzer 35 into an LED or LCD display that is configured in a bar graph arrangement with scaling corresponding to the interface pressures in increments of 10, depending on the measurement scale used, e.g., mmHg or kilopascals. Thresholds set in the signal processor determine the color of the bar graph. For example, where the pressure is below 25 mmHg, the color of the graph will be green. Between 25 and 40 mmHg, the bar(s) will be yellow, and above 40 mmHg the bar will be red. Multiple bars correspond to different regions as indicated by identified sensors or sensor combinations. The signal processor will store the detected pressure values in a memory and will record a time associated with each measured pressure value to generate a record of the patient's condition, when and how frequently elevated pressures were detected, and when and how the pressure was relieved, to help generate a patient management program.

In addition to the display generated by the processor, data may also be output to a printer at regular intervals, for example, every 24 hours, to produce a paper record for the patient's file, or electronically transferred to a computer storage medium or central network database on a continuous or regular periodic basis.

In a preferred embodiment, a set of algorithms is provided for continuous pressure monitoring based upon the Braden pressure ulcer risk analysis tool along with one or more clinical parameters related to the patient. As is known in the art, the Braden scale is used to generate a numeral score for predicting pressure ulcer risk based on factors including sensory perception, moisture, activity, mobility, nutrition and friction. A study done by researchers in Spain has determined that the Braden scale risk analysis sensitivity and specificity are 57.1% and 67.5%, respectively. (Pancoba-Hidalgo, et al., *J Adv. Nurs.* 2006 April; 54(1):94-110.) Other methods that can be used include the Norton scale and the Waterlow scale, however, these were found in the study to be less reliable than the Braden scale.

In addition to the Braden factors, other important factors involved in pressure ulcer risk include Spinal Cord Injury (SCI), advanced disease state, and prior history of pressure ulcers. Additional factors may include sedation, hypotension, history of arterial insufficiency (evidenced by leg pains or reduced pulses), age of patient, BMI (body mass index), recent hip or knee surgery, type of mattress (lack of pressure re-distribution surface, alternating pressure air mattress, or low pressure mattress, for example), diabetes, advanced cancer, skin lactic acid level, or loss of tissue turgor, perceived humidity of the sensor.

Figure 6A:
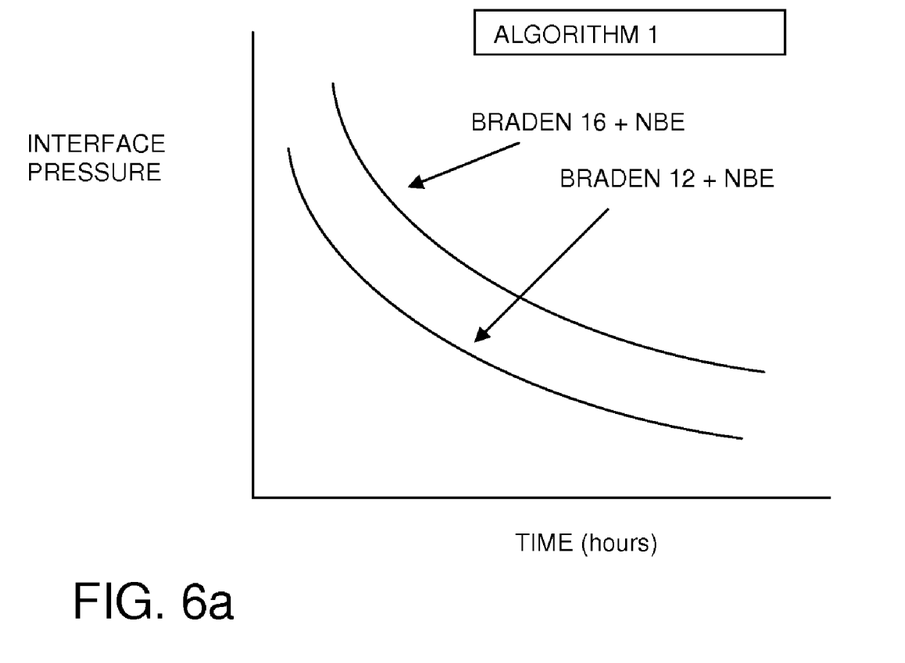
Figure 6B:
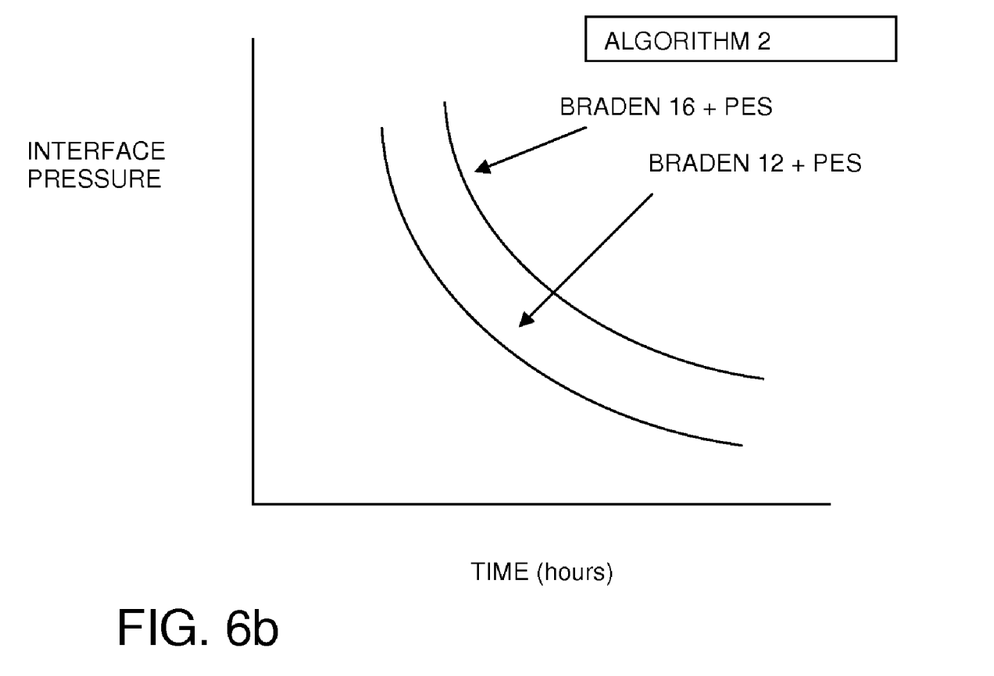
Figure 6C:
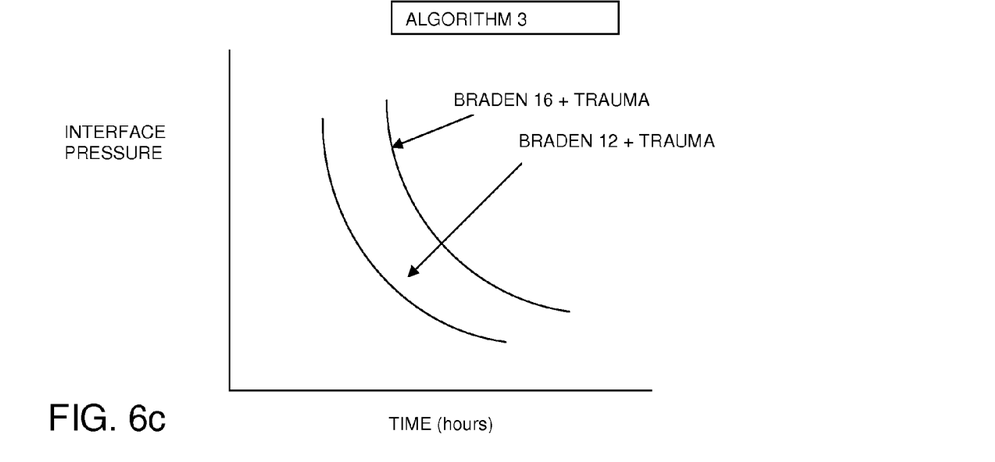
Figure 6D:
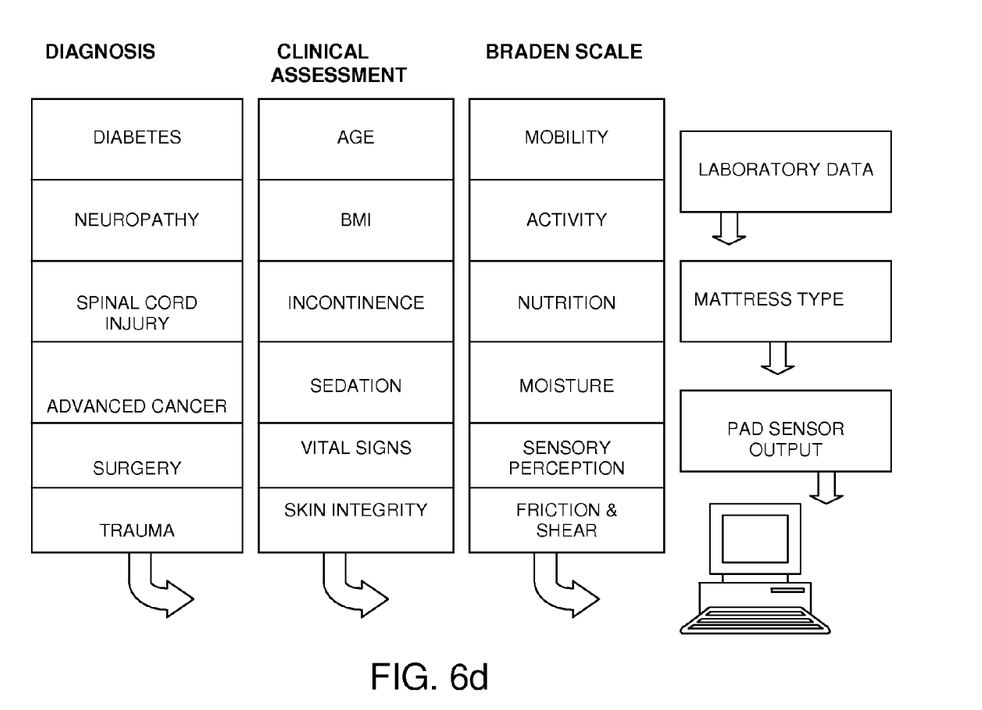
FIG. 6d is a diagram showing the data sources that may be used for creating and executing an algorithm for monitoring a patient.

The diagram provided in FIG. 6d identifies different possible data sources that can provide the information needed to accurately and repeatably calculate and monitor a patient's risk of developing ulcers. The first category of possible data points comes from the physician's assessment of the patient, i.e., diagnosis of a disease or condition. The second category comes from the clinical assessment process that occurs, for example, during patient intake. The third category uses the Braden scores—numerical values assigned during patient assessment according to the Braden scale. Laboratory data may also be considered, e.g., lactic acid levels, etc., as is mattress type and the data generated by the pressure sensors that are placed underneath the patient in a bed pad or other pad. Raw data from each of these sources is input into a supervised learning algorithm, such as a neural network, decision tree or support vector machine, that processes and classifies, i.e., "mines" the data, to identify patterns that may be used in supporting human decisions or for establishing custom monitoring criteria that are individually tailored for each patient. Such a process would include steps of data selection, pre-processing the data to clean and reconfigure it for processing, transforming the data into an optimal form for analysis, and pattern extraction. The analysis result is reported to the caregiver and/or stored within a database containing the patient's history.

To provide a few simple examples of how a monitoring algorithm can be applied, based upon the patient's Braden score and the other data, a time-interface pressure curve can be applied to generate indications that a caregiver's attention is required. FIGS. 7a-c provide three examples of curves. The sample curves in FIG. 6a are for a patient older than 65, who is frail, has not had immediate surgery, and is in a nursing home, homecare or in a hospital on a regular medical floor. In this case, the curves are based on 50% Braden weighted score and 50% non-blanchable erythema. Two different curves are shown, one for Braden score 16+NBE and one for Braden score 12+NBE. Because the lower score represents greater risk of developing ulcers, the amount of time that a patient is allowed to remain at a given interface pressure threshold will be less than a patient with a higher Braden score. In FIG. 6b, a second algorithm is used for an acute care setting, for example, in MICU, CCU, or when there is challenging fluid management issue. In this algorithm, Braden score is weighted 75% and pitting edema of the sacrum (PES) is weighted 25%. Again, there are two curves, one for Braden 16+PES, the other for Braden 12 and PES. Sample curves for a healthy young person with acute trauma are shown in FIG. 6c and are generated by a combination of the Braden scale and some other factor, e.g., nature of the injury, such as spinal cord injury or head trauma. When the measured pressure exceeds the threshold pressure as determined by the predictive algorithm, the system controller will generate an alarm or other indicator that attention is required.

While the preferred embodiments of the invention have been described, modifications can be made and other embodiments may be devised without departing from the spirit of the invention and the scope of the appended claims.

The invention claimed is:

1. A support surface for preventing pressure ulcers in a patient, the support surface comprising a multi-layer composite fabric comprising:
   a skin contact layer comprising a woven fabric of synthetic filament yarns woven to provide air permeability and moisture vapor permeability and having a thickness of less than 1 mm, the skin contact layer having an upper, skin contact surface and a bottom surface;
   an absorbent middle layer abutting the bottom surface of the skin contact layer, the middle layer comprising a breathable microfiber fabric woven from synthetic fibers having a cross-sectional shape that includes a plurality of voids for generating a capillary effect for moisture transition from an upper surface of the middle layer to a bottom surface of the middle layer, wherein the skin contact layer and the middle layer are stitched together using a stitching pattern that is optimized to produce an open pattern with minimal puckering;
   a bottom layer attached to the skin contact layer and the middle layer at a peripheral edge of each layer, the bottom layer comprising a breathable, waterproof fabric having a thickness of less that 1 mm that is woven from synthetic yarn to produce a moisture vapor transfer rate within the range of 5,000 to 20,000 grams per meter squared per 24 hours.

2. The support surface of claim 1, wherein the stitching pattern comprises a plurality of straight and curved lines, wherein no lines cross over other lines.

3. The support surface of claim 1, wherein the stitching pattern comprises a plurality of detached circles and a plurality of parallel lines, wherein the circles and parallel lines intersect within the pattern but do not cross.

4. The support surface of claim 3, wherein each circle has a diameter in the range of 25-50 mm.

5. The support surface of claim 3, wherein the parallel lines are separated by a distance in the range of 25-50 mm.

6. The support surface of claim 1, wherein the stitching pattern comprises a plurality of parallel wavy lines.

7. The support surface of claim 1, wherein a combined thickness of the skin contact layer, the middle layer and the bottom layer is within the range of 2 to 5 mm.

8. The support surface of claim 1, wherein the support surface is a bed pad and further comprising at least one hand grip disposed along at least one edge of the bed pad.

9. The support surface of claim 1, wherein the bottom layer is coated with a polyurethane.

10. The support surface of claim 1, further comprising an array of pressure sensors disposed beneath the bottom layer.

11. The support surface of claim 10, wherein the array of pressure sensors generate electronic signals for input into a computer monitoring system.

12. The support surface of claim 10, wherein the computer monitoring system includes software for determining a risk of pressure sore development in the patient based upon an algorithm that identifies a patient-specific pattern using a plurality of risk factors selected from the group consisting of medical diagnosis, clinical assessment, Braden scale, laboratory data, mattress type and the electronic signals generated by the array of pressure sensors.

13. The support surface of claim 12, wherein the computer monitoring systems generates an alarm when a pre-determined combination of risk factors according to the patient-specific pattern is present.

14. The support surface of claim 1, wherein the skin contact layer is treated with an anti-microbial finish.

15. A support surface for preventing pressure ulcers in a patient, the support surface comprising a multi-layer composite fabric comprising:
a skin contact layer comprising a woven fabric of nylon-polyester filament yarns woven to provide a pore size of 4 to 10 microns and having a thickness of less than 1 mm, the skin contact layer having an upper, skin contact surface and a bottom surface;
an absorbent middle layer abutting the bottom surface of the skin contact layer, the middle layer comprising a breathable microfiber fabric woven from polyester fibers having a cross-sectional shape that includes a plurality of channels for generating a capillary effect for moisture transition from an upper surface of the middle layer to a bottom surface of the middle layer, wherein the skin contact layer and the middle layer are stitched together with a tension and a stitch length that is optimized to produce minimal puckering;
a bottom layer attached to the skin contact layer and the middle layer at a peripheral edge of each layer, the bottom layer comprising a breathable, waterproof fabric coated with polyurethane and having a thickness of less that 1 mm that is woven from synthetic yarn to produce a moisture vapor transfer rate within the range of 5,000 to 20,000 grams per meter squared per 24 hours.

16. The support surface of claim 15, wherein the stitching pattern comprises a plurality of parallel lines, wherein no lines cross over other lines.

17. The support surface of claim 16, wherein each of the parallel lines is wavy.

18. The support surface of claim 15, wherein a combined thickness of the skin contact layer, the middle layer and the bottom layer is within the range of 2 to 5 mm.

19. The support surface of claim 15, wherein the support surface is a bed pad and further comprising at least one hand grip disposed along at least one edge of the bed pad.

20. The support surface of claim 15, further comprising an array of pressure sensors disposed beneath the bottom layer.

21. The support surface of claim 20, wherein the array of pressure sensors generate electronic signals for input into a computer monitoring system.

22. The support surface of claim 21, wherein the computer monitoring system includes software for determining a risk of pressure sore development in the patient based upon an algorithm that identifies a patient-specific pattern using a plurality of risk factors selected from the group consisting of medical diagnosis, clinical assessment, Braden scale, laboratory data, mattress type and the electronic signals generated by the array of pressure sensors.

23. The support surface of claim 22, wherein the computer monitoring systems generates an alarm when a pre-determined combination of risk factors according to the patient-specific pattern is present.

24. The support surface of claim 21, wherein the skin contact layer is treated with an anti-microbial finish.

* * * * *